(12) United States Patent
Unger et al.

(10) Patent No.: US 8,999,269 B2
(45) Date of Patent: Apr. 7, 2015

(54) DEVICE FOR STRETCHING SAMPLE SECTIONS

(71) Applicant: Leica Microsystems CMS GmbH, Wetzlar (DE)

(72) Inventors: Ralf Unger, Mittenaar-Bicken (DE); Frank Eisenkrämer, Biebertal (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 0 days.

(21) Appl. No.: 13/865,229

(22) Filed: Apr. 18, 2013

(65) Prior Publication Data
US 2013/0287649 A1 Oct. 31, 2013

(30) Foreign Application Priority Data
Apr. 25, 2012 (DE) .......................... 10 2012 206 796

(51) Int. Cl.
*A61B 10/00* (2006.01)
*G01N 1/06* (2006.01)
*G01N 1/28* (2006.01)

(52) U.S. Cl.
CPC ................ *G01N 1/06* (2013.01); *G01N 1/2813* (2013.01)

(58) Field of Classification Search
CPC .................................... G01N 1/06; B32B 1/00
USPC ................................. 422/536, 63–67; 436/180
See application file for complete search history.

(56) References Cited

U.S. PATENT DOCUMENTS

| 5,993,634 | A  | * | 11/1999 | Simpson et al. | ............... 204/612 |
| 6,705,187 | B2 | * | 3/2004  | Konrad         | ............... 83/13   |
| 2002/0038590 | A1 |   | 4/2002  | Konrad         |                       |
| 2007/0048509 | A1 | * | 3/2007  | Yoneyama et al.| ........... 428/212   |

FOREIGN PATENT DOCUMENTS

| DE | 2732001 C2       | 2/1979  |
| DE | 10013688 A1      | 10/2001 |
| DE | 10013693 B4      | 10/2001 |
| DE | 202010011369 U1  | 12/2010 |
| GB | 1058696          | 2/1967  |

* cited by examiner

*Primary Examiner* — Jyoti Nagpaul
(74) *Attorney, Agent, or Firm* — Hodgson Russ LLP

(57) ABSTRACT

The present invention relates to a glass plate (2) for use in a device (1) for stretching sample sections having a sectioning knife, the glass plate (2) being arranged at the back (3) of the sectioning knife in such a way that a defined gap (4) for reception of the sectioned sample is formed between the back (3) of the sectioning knife and the plate (2), the glass plate (2) possessing, at least on one of its longitudinal sides (21, 22), edges (211, 212; 221, 222) ground and polished to optical flatness.

5 Claims, 3 Drawing Sheets

DEVICE FOR STRETCHING SAMPLE SECTIONS

CROSS REFERENCE TO RELATED APPLICATIONS

Figure 1:
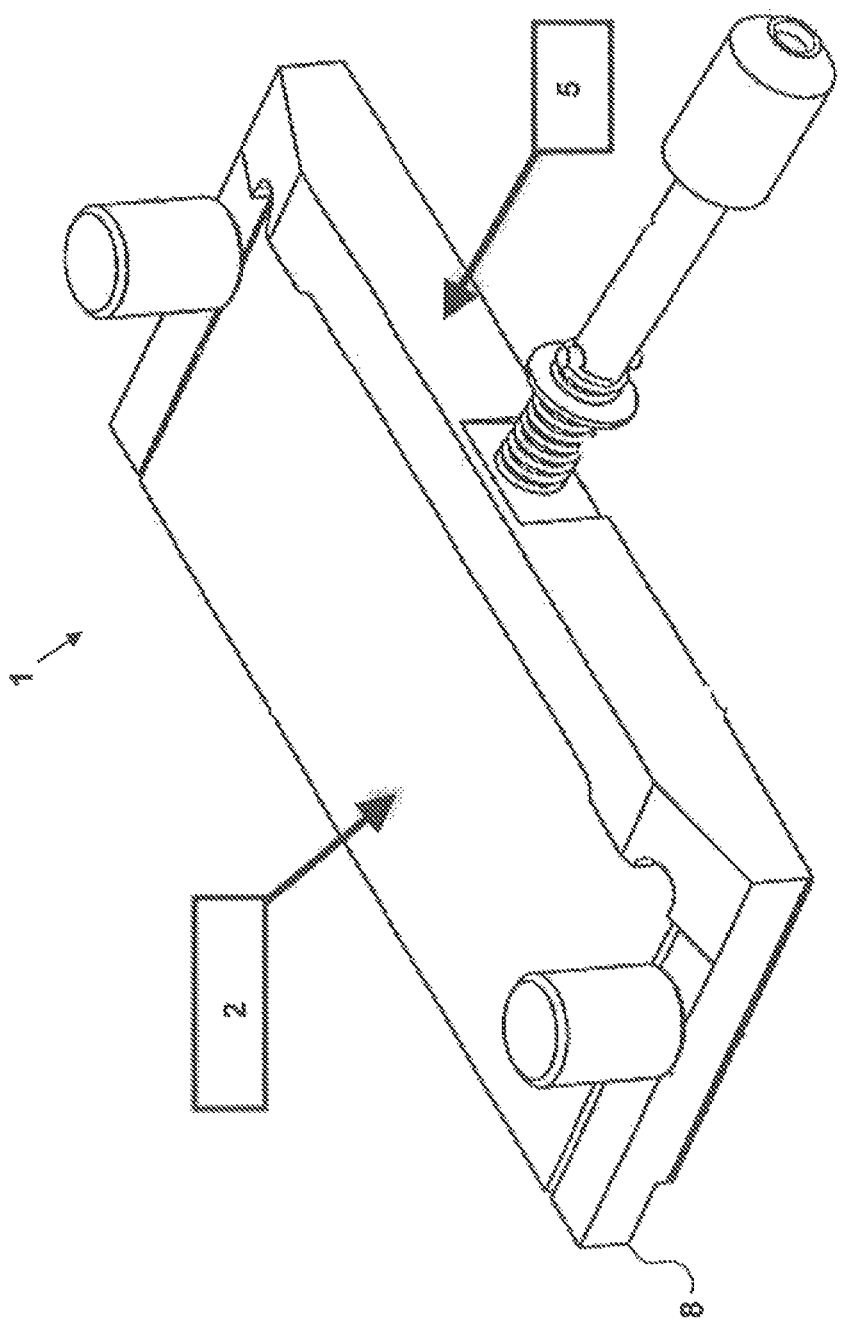

This application claims priority of German patent application number 10 2012 206 796.5 filed Apr. 25, 2012, the entire disclosure of which is incorporated by reference herein.

FIELD OF THE INVENTION

The present invention relates to a device for stretching sample sections (a section stretcher) of a type having a sectioning knife and a glass plate arranged at the back of the sectioning knife in such a way that a defined gap is formed between the back of the sectioning knife and the glass plate for reception of the sectioned sample (2).

BACKGROUND OF THE INVENTION

So-called "section stretchers," or devices for stretching sample sections, are known from the existing art of microtomes. Microtomes serve for the production of thin sections of various prepared samples, such as tissue specimens, in medicine or biology. Such samples either can be sectioned while frozen, or are embedded into an embedding medium (usually paraffin) and sectioned together with it. Extremely sharp knives that are secured in a knife holder are used to section the samples. The thickness of the thin sections is generally in the micrometer range, while typical lengths and widths are in the range from 5 mm to 30 mm. The sample sections are usually mounted onto a specimen slide so they can then be investigated microscopically. The sections tend to roll up upon sectioning. Rolled-up sample sections are, however, very difficult to mount onto a specimen slide, and the risk also exists that the rolled-up sample sections may break. The risk of breakage also exists if a manual attempt is made to grasp the section with a brush or a forceps and pull it away from the knife blade in order to prevent rolling.

So-called "section stretchers," or section stretching devices, are used in order to prevent the sample sections from undesirably rolling up. Section stretchers comprise a glass plate or Plexiglas plate that is arranged at the knife back, parallel to and at a short distance from the knife blade, so that a thin gap is produced between the knife back and the plate. The "knife back" is understood as that part of the knife which is adjacent to the knife blade (also called the "edge" or "bevel") and slides over the sample section before it detaches from the sample. During sectioning, the sectioned sample thus pushes into the gap between the glass plate or Plexiglas plate and the aforesaid knife back.

After sectioning, the section stretcher is removed from the knife back and the sectioned sample is removed. In the case of cryostat sectioning, this removal is effected by the fact that a specimen slide warmed to room temperature is placed against the knife edge and slowly lowered onto the sectioned sample. Upon contact, the ice in the sample abruptly melts and the sectioned sample remains adhered onto the specimen slide.

DE 100 48 724 B4 discloses a device for stretching cryostat sections, having a section stretcher described above. The gap between the plate and knife back is typically 0.15 mm. In this document, this gap is embodied in defined fashion by the fact that the glass plate or Plexiglas plate is mounted in a frame that comprises internally shaped-on struts. The struts are equipped with a support surface for the plate. The frame further comprises an abutment edge for placement of the frame onto the back surface of the sectioning knife. The spacing between said abutment edge and the support surface for the plate then forms the defined gap for reception of the sectioned sample, which is effectively prevented from rolling up. A further result of this embodiment of the section stretcher is that no further contact occurs between the sensitive plate and the sectioning knife. The dimension of the gap is furthermore no longer dependent on the material thicknesses of the plates, but instead is defined unequivocally by the spacings on the frame. Plates of different material thicknesses can thus also be used, with no change in the dimension of the gap.

With regard to further details of the manner of operation and the configuration of the section stretcher or the corresponding device for stretching cryostat sections, reference may be made explicitly to the aforementioned DE 100 48 724 B4 in its entirety. For purposes of disclosure, the content of this patent is assumed to be incorporated into the present application.

Another device for stretching sample sections is known from DE 20 2010 011 369 U1. Here the section stretcher serves at the same time as a finger protector for an operator who is manually removing the sample section from the knife back. What is proposed is a part or member, triangular in section and extending over the length of the knife blade, that is arranged at a specific distance from the sample and at a specific distance from the knife back. The depth of the gap existing with respect to the knife back is dimensioned in such a way that rolling of the section is prevented, but on the other hand the depth of the gap is at most such that sections of a usual dimension emerge from the gap, in the course of the sectioning motion, with their front side in the flow direction. The height of the gap here is typically between 0.15 mm and 0.25 mm, while the depth of the gap is between 3 mm and 5 mm.

Another type of section stretcher is known from DE 27 32 001 C2. Here the section stretcher is retained by magnetic force, which is said to ensure unequivocal and reproducible retention as well as consistent gap widths.

DE 100 13 693 B4 relates to a method for manufacturing a section stretcher plate from inorganic glass. This document mentions the previous practice of grinding and polishing the edge lines of a glass plate that were obtained by bending fracture. As stated in this document, however, the high edge quality of the edge lines would be affected by the grinding and polishing. To prevent this, the teaching of this document provides for controlled rounding in the course of a subsequent thermal or chemical step. In thermal rounding, for example, each edge line is processed with a $CO_2$ laser, with the result that the edge line is slightly melted and edge rounding occurs. In chemical rounding, the edge line to be rounded is immersed into a chemical bath in which, for example, potassium ions are dissolved. Hardening is simultaneously achieved thereby.

GB 1,058,696 A discloses coating a section stretching glass plate with a plastic material such as PTFE that is sintered onto the surface of the glass plate.

Lastly, DE 100 13 688 A1 discloses a method for manufacturing a section stretcher plate made of inorganic glass, in which the section stretcher plate is detached from a glass surface substrate, by means of stresses thermally induced in that glass surface substrate, along a detachment line that corresponds to the lateral edge of the section stretcher plate.

It has become apparent that in a device for stretching cryostat sections in accordance with DE 100 48 724 B4 already discussed, it is advantageous to use glass plates in the section stretcher, since glass plates, in contrast to Plexiglas plates, scratch less easily and do not acquire an appreciable static charge when used. Chemical resistance (for example in the context of cleaning, or upon contact with the sample section) is also greater, so that glass plates less quickly become opaque or "blind". It has furthermore become apparent that sample sections can get caught, or become shredded, on the edges of the glass plates.

An object of the present invention is therefore to optimize glass plates used in section stretchers of the kind recited previously in order to eliminate the aforementioned disadvantages in the context of the sectioning of samples.

SUMMARY OF THE INVENTION

The invention relates to a glass plate for use in a device for stretching sample sections, and to such a device for stretching sample sections having a sectioning knife and such a glass plate, the glass plate being arranged at the back of the sectioning knife in such a way that a defined gap for reception of the sectioned sample is formed between the back of the sectioning knife and the plate. The glass plate possesses, at least on one and in particular on two oppositely located longitudinal sides, edges ground and polished to optical flatness, having an optical flatness better than $\lambda/2$ and/or a roughness <5 nm RMS.

Further advantages and embodiments of the invention may be gathered from the respective dependent claims and from the description below, and from the appended drawings.

ADVANTAGES OF THE INVENTION

Grinding of the edges with an optical grinding medium (lapping with loose grit and grinding with bound grit), and polishing of the edges with an optical polishing agent and a polishing base in an optically flat manufacturing process, makes it possible to generate both edges of one longitudinal side of the glass plate with a high optical flatness better than $\lambda/2$ and minimal roughness (<5 nm RMS).

It has been found that with the edges ground and polished according to the present invention, catching of the sample sections or shredding of the sample sections on an edge of the glass plate is almost entirely absent. Both edges of a longitudinal side can be used alternately (by turning the glass plate). Optically flat grinding and polishing of the edges of both longitudinal sides of the glass plate makes a total of four edges available for use in the section stretcher.

A so-called float glass can be used as a glass for the glass plates according to the present invention. In known float glass manufacture, the purified molten glass, which is viscous at more than 1000° C., is continuously directed from one side onto an elongated bath of molten tin, on which the molten glass spreads uniformly as a film. Very smooth surfaces form, and the glass that has solidified at the cooler end (still at a temperature of approx. 600° C.) is continuously pulled off and cooled in stress-free fashion in a cooling oven. The glass plates are generally cut out of a stack of (float) glass panels cemented to one another. Grinding and polishing of the edges then occurs in an optically flat manufacturing process through which only prisms, beam splitters, wedge plates, filters, and other similar components usually pass. As indicated above, extremely high flatness values and extremely low roughness values can be achieved in this manufacturing process.

A further or alternative optimization of the glass plates according to the present invention can be achieved by hardening. For this, the glass plates are heated briefly to the relevant so-called transformation temperature $T_g$, and then rapidly cooled in a stream of air. For glass plates made of float glass, $T_g$ is usually 525° C. to 533° C. and the cooling rate is >5° C./hour, as opposed to the usual precision cooling rate of ≤2° C./hour.

Glass items hardened in this manner are more robust and more durable.

Additionally or alternatively, the glass plate can be optimized by equipping it with a protective layer acting as a diffusion barrier. It has been found that, in particular, glass plates made of float glass lose their optical transparency, and partly discolor, because foreign substances diffuse in. The optical transparency can be maintained by vapor-depositing a diffusion barrier made of dielectric materials, preferably metal oxides, onto the surface of the glass plate.

The glass plate can furthermore be additionally or alternatively optimized by being finished with a reflection-reducing layer. The reflection-reducing layer can be applied, in particular, after application of the protective layer acting as a diffusion barrier. Suitable reflection-reducing layers are those used, for example, for objectives or eyepieces. A $\lambda/4$ layer of magnesium fluoride is often used. Multiple finishing using multiple layers having different indices of refraction can also be used. Layer systems designed, in terms of the selection of thickness and material, so that a reflection-reducing effect occurs are typical. Appropriate materials are fluorides and metal oxides, which are applied as dielectric layers.

The invention further relates to a device for stretching sample sections, in particular cryostat sections, having a sectioning knife and having a glass plate according to the present invention that is arranged at the back of the sectioning knife in such a way that a defined gap for reception of the sectioned samples is formed between the back of the cutting knife and the plate.

One possible embodiment of such a device is known per se from the patent DE 100 48 724 B4 already discussed in the introduction to the description. Use of the glass plate according to the present invention in the device discussed therein for stretching cryostat sections is preferred.

It is understood that the features recited above and those yet to be explained below are usable not only in the respective combination indicated, but also in other combinations or in isolation, without departing from the scope of the present invention. The right is reserved, in particular, to place the aforementioned additional or alternative optimizations of the glass plate respectively under individual protection.

The invention is schematically depicted in the drawings on the basis of an exemplifying embodiment, and will be described in detail below with reference to the drawings.

BRIEF DESCRIPTION OF THE DRAWING VIEWS

Figure 2:
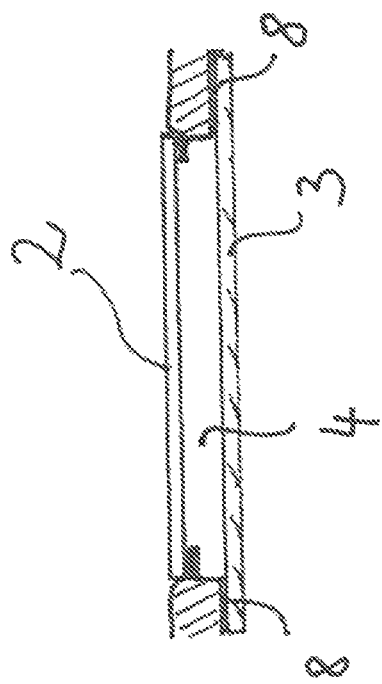
Figure 3:
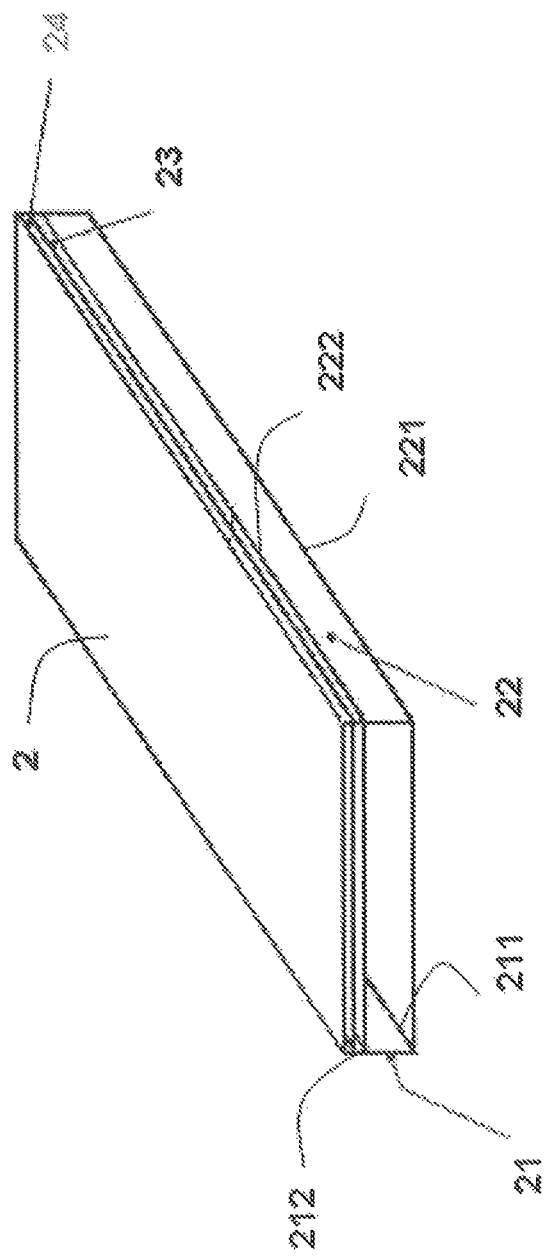

FIG. 1 schematically shows a device 1 for stretching sample sections (section stretcher), as used advantageously for the present invention;

FIG. 2 schematically shows the configuration of a gap between the glass plate and knife back with a device according to FIG. 1; and FIG. 3 schematically shows a glass plate according to the present invention for a device according to FIG. 1.

DETAILED DESCRIPTION OF THE INVENTION

Device 1 (hereinafter referred to as a "section stretcher") according to FIG. 1 is known from German patent DE 100 48 724 B4 already discussed above. FIG. 1 derives from that patent, so that explicit reference will be made in supplementary fashion to said patent regarding further details. The configuration and manner of operation of section stretcher 1 will therefore be discussed below only to the extent necessary for an understanding of the present invention.

Section stretcher 1 comprises a holder 5 for a glass plate 2. Glass plate 2 in turn rests on support struts that extend along the inner side of the U-shaped holder 5. Abutment edge 8 serves for abutment of section stretcher 1 against the back surface of a sectioning knife (not depicted here). Section stretcher 1 can be fastened on a knife holder (not depicted) of a microtome.

FIG. 2 schematically shows holder 5, resting on back 3 of a sectioning knife, with glass plate 2. Abutment edge 8 of holder 5 rests on back surface 3 of the sectioning knife. The spacing between abutment edge 8 and the support surface or underside of glass plate 2 forms the defined gap 4 for reception of the sectioned sample. The sample section travels into gap 4 during sectioning of the sample, thereby preventing it from rolling up. Gap 4 typically has a height of 0.15 mm.

FIG. 3 shows an embodiment of a glass plate 2 according to the present invention. Glass plate 2 possesses two longitudinal sides 21 and 22; the longitudinal sides, but in particular the edges of the longitudinal sides, are ground and polished to optical flatness. In order to effectively prevent shredding and/or catching of the sample sections on the edges of the glass plates, that edge 221 of glass plate 2 which faces gap 4 (see FIG. 2) is ground and polished to optical flatness. The flatness is better than $\lambda/2$, and roughness is less than 5 nm RMS. It is useful to grind and polish all four edges 221, 222, and 211, 212 of the two longitudinal sides 22 and 21, respectively, of glass plate 2 in an optically flat manufacturing process. The result is that four edges of glass plate 2 are available, and can be used to form gap 4 of FIG. 2 by correspondingly turning or rotating glass plate 2.

An additional (or also alternative) form of optimizing glass plate 2 consists in heating glass plate 2 to the aforementioned transformation temperature $T_g$ and then rapidly cooling it in a stream of air. Glass plates hardened in this fashion are more robust and more durable.

A further additional (or also alternative) form of optimization consists in equipping glass plate 2 on at least one side with a protective layer 23 acting as a diffusion barrier. This protective layer 23 prevents foreign substances, which might result in discoloration and/or clouding of the glass plate, from diffusing in.

Glass plate 2 depicted in FIG. 3 furthermore possesses a reflection-reducing layer 24 that is applied onto protective layer 23. Glass plate 2 optimized in this fashion permits optimum optical viewing of the sectioning process without troublesome reflections, glass plate 2 being protected from scratching, from discoloration, and from a decrease in optical transparency.

PARTS LIST

1 Section stretcher
2 Glass plate
3 Knife back
4 Gap
5 Holder
8 Abutment edge
21, 22 Longitudinal sides
23 Protective layer (diffusion barrier)
24 Anti-reflection layer
211, 212 Edges
221, 222 Edges

What is claimed is:

1. A device (1) for stretching sample sections, the device comprising:
    a sectioning knife having a back (3);
    a glass plate (2) arranged at the back (3) of the sectioning knife in such a way that a defined gap (4) for reception of a sample section is formed between the back (3) of the sectioning knife and the plate (2);
    wherein the glass plate (2) comprises a first longitudinal side (21) having a first pair of longitudinal edges (211, 212) and a second longitudinal side (22) having a second pair of longitudinal edges (221, 222), wherein the longitudinal edges of at least one of the first pair of longitudinal edges (211, 212) and the second pair of longitudinal edges are ground and polished to optical flatness, having a roughness <5 nm RMS.

2. The device according to claim 1, wherein the first pair of longitudinal edges (211, 212) and the second pair of longitudinal edges (221, 222) are ground and polished to have a roughness <5 nm RMS.

3. The device according to claim 1, wherein the glass plate (2) is hardened by thermal stress introduction.

4. The device according to claim 1, wherein the glass plate (2) has a protective layer (23) acting as a diffusion barrier.

5. The device according to claim 1, wherein the glass plate (2) is finished with a reflection-reducing layer (24).

* * * * *